US 6,458,375 B1
Oct. 1, 2002

(54) MALLEABLE PASTE WITH ALLOGRAFT BONE REINFORCEMENT FOR FILLING BONE DEFECTS

(75) Inventors: Arthur A. Gertzman, Stony Point, NY (US); Moon Hae Sunwoo, Old Tappan, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 0 days.

(21) Appl. No.: 09/677,891

(22) Filed: Oct. 3, 2000

Related U.S. Application Data

(63) Continuation-in-part of application No. 09/515,656, filed on Feb. 29, 2000, which is a continuation-in-part of application No. 09/031,750, filed on Feb. 27, 1998, now Pat. No. 6,030,635.

(51) Int. Cl.$^7$ .................................................. A61F 2/00
(52) U.S. Cl. ....................... 424/423; 424/422; 424/426; 424/484; 424/488
(58) Field of Search ............................ 623/23.61, 23.62, 623/23.63; 424/422, 423, 488, 400

(56) References Cited

U.S. PATENT DOCUMENTS

| | | |
|---|---|---|
| 4,172,128 A | 10/1979 | Thiele et al. |
| 5,290,558 A | 3/1994 | O'Leary et al. |
| 5,314,476 A | 5/1994 | Prewett et al. |
| 5,356,629 A * | 10/1994 | Sander et al. ............... 523/113 |
| 5,516,532 A | 5/1996 | Atala et al. |
| 5,830,493 A | 11/1998 | Yokota et al. |
| 6,340,477 B1 | 1/2002 | Anderson |

FOREIGN PATENT DOCUMENTS

| | | |
|---|---|---|
| EP | 0 522569 A1 | 1/1993 |
| EP | 0 784985 A1 | 7/1997 |
| WO | WO 98/14222 | 4/1998 |
| WO | WO 99/11298 | 3/1999 |
| WO | WO 99/52572 | 10/1999 |

OTHER PUBLICATIONS

Rubin—Biomaterials in Reconstructive Surgery 1978 pp. 314,315.*
T. Sasaki Et Al. Bone vol. 1 (16) No. 1 Jan. 1995 (9–15).*

* cited by examiner

*Primary Examiner*—Thurman K. Page
*Assistant Examiner*—Liliana Di Nola-Baron
(74) *Attorney, Agent, or Firm*—John S. Hale; Gipple & Hale

(57) ABSTRACT

The invention is directed toward a sterile malleable bone composition for application to a bone defect site to promote new bone growth at the site comprising a mixture of demineralized osteogenic bone powder with a particle size ranging from about 250 to about 750 microns and surface demineralized cortical bone rods having a diameter ranging from 1.0 mm to 5.00 mm or larger bone chips. The surface demineralized cortical bone rods have diameter to length ratio ranging from 1:2 to 1:20. The demineralized bone powder range from about 25 to about 30% of the weight of the composition and the cortical bone rods range from 5% to about 10% of the weight of the composition with the carrier being selected from the high molecular weight hydrogel in aqueous solution having a high molecular weight over 700,000 Daltons and ranging from about 2.0% to about 5.0% by weight of the carrier solution.

49 Claims, 1 Drawing Sheet

MALLEABLE PASTE WITH ALLOGRAFT BONE REINFORCEMENT FOR FILLING BONE DEFECTS

RELATED APPLICATION

The present invention is a continuation-in-part of U.S. patent application Ser. No. 09/515,656 filed Feb. 29, 2000 which is a continuation-in-part of U.S. patent application Ser. No. 09/031,750, now U.S. Pat. No. 6,030,635 issued Feb. 27, 1998.

FIELD OF INVENTION

The present invention is generally directed toward a surgical bone product and more specifically is a malleable putty containing demineralized allograft bone particles and mineralized chips and/or rods mixed in a fluid carrier having an isotonic phosphate buffer and a high molecular weight viscous excipient derived from the class of biomaterials known as hydrogels.

BACKGROUND OF THE INVENTION

Surgical implants should be designed to be biocompatible in order to successfully perform their intended function. Biocompatibility may be defined as the characteristic of an implant acting in such a way as to allow its therapeutic function to be manifested without secondary adverse affects such as toxicity, foreign body reaction or cellular disruption.

Malleable bone putty is used to correct surgical defects that may be caused by trauma, pathological disease, surgical intervention or other situations where defects need to be managed in osseous surgery. It is important to have the defect filler in the form of a stable, viscous putty to facilitate the placement of the bone growth medium into the surgical site which is usually uneven in shape and depth. The surgeon will take the putty on a spatula or other instrument and trowel it into the site or take it in his/her fingers to shape the bone inducing material into the proper configuration to fit the site being corrected.

For over fifty years, surgeons have been using cancellous cubes mixed with blood and bone marrow as a form of putty. A number of premixed products presently exist to treat this surgical need. One example is autologous bone segments recovered from the patient which can be ground into bone granules. When the bone segments are removed from the patient, they are wet and viscous from the associated blood. This works very well to heal the defect but requires significant secondary surgery resulting in lengthening the surgery, extending the time the patient is under anesthesia, extending the recovery time and increasing the cost. In addition, a significant increase in patient morbidity is attendant in this technique as the surgeon must take bone from a non-involved site in the patient to recover sufficient healthy bone, marrow and blood to perform the defect filling surgery. This leads to significant post-operative pain.

Another product being used involves the use of inorganic materials to provide a matrix for new bone to grow at the surgical site. These inorganic materials include hydroxyapatite obtained from sea coral or derived synthetically. Either form may be mixed with the patient's blood and/or bone marrow to form a putty. Calcium sulfate or plaster of Paris may also be mixed with water to similarly form a putty. These inorganic materials are osteoconductive but are bio-inert and do not absorb or become remodeled into natural bone. They consequently remain in place indefinitely as a brittle, foreign body in the patient's bone tissue.

Another prior art product is the formulation of demineralized allograft bone particles in collagen. Both bovine and human collagen have been used for this application. Bovine collagen carries the risk of an immunogenic reaction by the recipient patient. Recently, it has been found that a disease of cattle, bovine spongioform encephalopathy (BSE) can be transmitted from bovine tissue to humans. Thus, bovine tissue carries a risk of disease transmission and is not a desirable carrier for allograft tissue.

Human collagen is free of these animal based diseases. However, collagen absorbs slowly in the human body, particularly in a bony site which usually has a low degree of vascularity. The slow absorption of collagen can delay the growth of new bone and result in the formation of scar tissue at the site. This could result in a non-bony healing and a result with much less tensile strength.

Allograft bone is a logical substitute for autologous bone. It is readily available and precludes the surgical complications and patient morbidity associated with obtaining autologous bone as noted above. Allograft bone is essentially a collagen fiber reinforced hydroxyapatite matrix containing active bone morphogenic proteins (BMP) and can be provided in a sterile form. The demineralized form of allograft bone is naturally both osteoinductive and osteoconductive. The demineralized allograft bone tissue is fully incorporated in the patient's tissue by a well established biological mechanism. It has been used for many years in bone surgery to fill the osseous defects previously discussed.

It is also well known in the art that for several decades surgeons have used a patient's own blood as a vehicle in which to mix the patient's bone chips or bone powder, or demineralized bone powder so as to form a defect filling paste. Blood is a useful carrier because it is available from the bleeding operative site, is non-immunogenic to the patient and contains bone morphogenic proteins which facilitate wound healing through new bone growth. However, stored blood from other patients has the deficiencies that any blood transfusion would have such as blood type compatibility, possibility of transmission of disease and unknown concentration of BMP which are to some extent dependent upon the age of the donor.

While blood contains from forty percent (40%) to fifty percent (50%) cell mass, it is a satisfactory carrier for demineralized bone powder because it contains both mono- and polysaccharides which contribute to the blood viscosity and provide the bulk viscosity to the paste created by mixing the bone powder and blood. Specific monosaccharides in blood are glucose at a concentration of 60–100 mg/100 ml (0.1%) and polysaccharides such as hexose and glucosamine at approximately 0.1%. Glucuronic acid is also present at approximately 0.4–1.4 mg/100 ml (average 0.01%).

The problems inherent with using the patients blood as a carrier for demineralized bone powder are the difficulties of mixing the same at the operating site, the difficulty in obtaining a bone paste consistency which can be easily applied to the surgical area, the guesswork in mixing a usable composition at the site and the problem of having a bone paste which will promote optimum bone replacement growth and not be carried away by the body fluids at the operation site or simply fall out of the bone defect site. In an attempt to solve these and other problems, there have been a number of other attempts using other alternative mixtures and compositions.

A number of bone defect fillers currently being used are composed of demineralized bone matrix in the form of ground bone particles or very small bone fibers. The demineralized bone matrix is mixed in a carrier such as glycerol to create a viscous mass suitable for filling bone defects.

Demineralized allograft bone is usually available in a lyophilized or freeze dried and sterile form to provide for extended shelf life. The bone in this form is usually very coarse and dry and is difficult to manipulate by the surgeon. One solution to use such freeze dried bone has been provided in the form of a commercially available product, GRAFTON®, a registered trademark of Osteotech Inc., which is a simple mixture of glycerol and lyophilized, demineralized bone powder of a particle size in the range of 0.1 cm to 1.2 cm (1000 microns to 12,000 microns) as is disclosed in U.S. Pat. No. 5,073,373 forming a gel. Another version of this product from Osteotech, Inc. is a putty, which uses small bone fibers or shards produced by turning bone shafts on a lathe device to form shreds of bone. The small fibrous bone turnings created by the cutting tool are added to glycerol and form a swollen and tangled mass.

The GRAFTON® bone product works well to allow the surgeon to place the allograft bone material at the site. However, the carrier, glycerol has a very low molecular weight (92 Daltons) and is very soluble in water, the primary component of the blood which flows at the surgical site. Glycerol also experiences a marked reduction in viscosity when its temperature rises from room temperature (typically 22° C. in an operating room) to the temperature of the patient's tissue, typically 37° C. This combination of high water solubility and reduced viscosity causes the allograft bone material to be "runny" and to flow away from the site almost immediately after placement; which prevents the proper retention of the bone putty within the site as carefully placed by the surgeon.

These problems with GRAFTON® product have been attempted to be resolved by using a much larger particle size of allograft bone, specifically lamellae or slivers of bone created by milling or slicing the bone before mixing it with the glycerol carrier. This improves both the bulk viscosity and the handling characteristics of the mixture but still leaves the problem of the fast rate of dissipation of the carrier and some bone material due to the solubility of the glycerol carrier. The larger slivers of demineralized bone may also retard the development of new bone by the patient because the large bony lamellae do not pack as well as the smaller grainy particles of bone. This will leave more open space and could lengthen the time required to grow new bone and properly fill the defect. Another deficiency of using the bony lamellae is that the ends of the bony fragments are uneven and when packed into the surgical defect, leave uneven filaments of bone protruding out from the defect which can compromise the healing rate and present uneven surface areas of bone growth.

A recent version of GRAFTON® product uses relatively large demineralized particles in the carrier to create a heterogenous mixture which provides body or substance to the composition. This material is useful in filling larger defects where some degree of displacement resistance is need by the filler. Unfortunately this form of defect filler is not without problems in its surgical application. The glycerol carrier, common to all GRAFTON® product formulation is highly soluble in water. As previously noted, when applied in surgery, it is exposed to flowing blood, other body fluids and often, irrigation of the site by the surgeon, using large amounts of saline or sterile water. These fluids will wash away the glycerol and at least some of the demineralized bone matrix, resulting in a loss of the demineralized bone matrix at the site where it is needed.

Another new form from Regeneration Technologies, Inc.® utilizes corticocancellous chips dispersed in a thermoplastic demineralized bone matrix. Marketed as Opte-Form 100 HT™, it is a uniform particle size corticocancellous chip mass delivered in a thermoplastic polymer which must be warmed to 43–49° C. to be malleable. After packing into the wound, it becomes solid after cooling to reach body temperature (37° C.). This material uses uniformly sized chips which leave unfilled space between them, thus not providing a maximal amount of demineralized bone and retarding bone healing. Also, the need to warm the formulation before use is a considerable inconvenience in the operating room.

The prior art discloses a number of demineralized bone products. U.S. Pat. No. 5,290,558 discloses a flowable demineralized bone powder composition using a osteogenic bone powder with large particle size ranging from about 0.1 to about 1.2 cm. mixed with a low molecular weight polyhydroxy compound possessing from 2 to about 18 carbons including a number of classes of different compounds such as monosaccharides, disaccharides, water dispersible oligosaccharides and polysaccharides.

The advantages of using the bone particle sizes as disclosed in the U.S. Pat. No. 5,073,373 patent previously discussed were compromised by using bone lamellae in the shape of threads or filaments and still retaining the low molecular weight glycerol carrier. This later prior art is disclosed in U.S. Pat. Nos. 5,314,476 and 5,507,813 and the tissue forms described in these patents are known commercially as the GRAFTON® Putty and Flex, respectively.

The use of the very low molecular weight glycerol carrier also requires a very high concentration of glycerol to be used to achieve the bulk viscosity. Glycerol and other similar low molecular weight organic solvents are toxic and irritating to the surrounding tissues. Furthermore glycerol has been reported to be specifically neurotoxic and this problem is compounded when the concentration of glycerol is at the 20–95% level as disclosed in the U.S. Pat. No. 5,073,373 patent and the same is placed in a patient.

U.S. Pat. No. 5,356,629 discloses making a rigid gel in the nature of a bone cement to fill defects in bone by mixing biocompatible particles preferably polymethylmethacrylate coated with polyhydroxyethylmethacrylate in a matrix selected from a group which lists hyaluronic acid to obtain a molded semi-solid mass which can be suitably worked for implantation into bone. The hyaluronic acid can also be utilized in monomeric form or in polymeric form preferably having a molecular weight not greater than about one million Daltons. It is noted that the nonbioabsorbable material which can be used to form the biocompatible particles can be derived from xenograft bone, autologous bone, autogenous bone as well as other materials. The bioactive substance can also be an osteogenic agent such as demineralized bone powder, in addition to morselized cancellous bone, aspirated bone marrow and other autogenous bone sources. The average size of the particles employed is preferably about 0.1 to about 3.0 mm, more preferably about 0.2 to about 1.5 mm, and most preferably about 0.3 to about 1.0 mm. It is inferentially mentioned but not taught that particles having average sizes of about 7,000 to 8,000 microns, or even as small as about 100 to 700 microns can be used. However, the biocompatible particles used in this reference are used in a weight ranging from 35% to 70%. This is simply a cement used for implantation of hip prosthesis and is not used to promote bone growth.

U.S. Pat. No. 5,830,493 is directed toward a composite porous body (hyaluronic acid listed in a group of compounds) comprising a porous frame and a surface layer comprising a bioabsorbable polymer material formed on the surface. A bone morphogenetic protein (BMP) is carried on the surface and inside of the composite porous body. There is no demineralization of bone and the reference appears only to be relevant to show the addition of BMP to a bone forming graft.

Another attempt to solve the bone composition problem is shown in U.S. Pat. No. 4,172,128 which discloses demineralized bone material mixed with a carrier to reconstruct tooth or bone material by adding a mucopolysaccharide to a mineralized bone colloidal material. The composition is formed from a demineralized coarsely ground bone material, which may be derived from human bones and teeth, dissolved in a solvent forming a colloidal solution to which is added a physiologically inert polyhydroxy compound such as mucopolysaccharide or polyuronic acid in an amount which causes orientation when hydrogen ions or polyvalent metal ions are added to form a gel. The gel will be flowable at elevated temperatures above 35° C. and will solidify when brought down to body temperature. Example 25 of the '128 patent notes that mucopolysaccharides produce pronounced ionotropic effects and that hyaluronic acid is particularly responsible for spatial cross-linking. This bone gel is difficult to manufacture and requires a premolded gel form.

U.S. Pat. No. 4,191,747 teaches a bone defect treatment with coarsely ground, denatured bone meal freed from fat and ground into powder. The bone meal is mixed with a polysaccharide in a solution of saline and applied to the bone defect site.

Accordingly, the prior art as embodied in the glycerol and other carrier based technology to deliver demineralized allograft bone to a surgical osseous site is replete with problems and only partially addresses the problems inherent in correcting surgical defects.

SUMMARY OF THE INVENTION

The subject formulation is a complex mixture of demineralized and mineralized bone matrix and a viscous hydrogel having a high molecular weight material with a sodium based phosphate buffer acting as a carrier or delivery vehicle for the therapeutic agent, demineralized and mineralized bone matrix. The viscous formulation is designed to present the bone matrix, and its bone morphogenetic proteins (BMP). The macrostructure of the highly porous bone matrix itself serves both as an osteoconductive matrix and to signal the patient's tissue and cells to initiate the growth of new bone (osteoinduction). The formulation can be used in contact with bleeding bone. This condition is created either from trauma or a surgical procedure, that may involve drilling, sawing, grinding or scraping the bone to achieve a bleeding condition. In surgery, the bone is traumatized or surgically cut exposing blood capillaries, Haversian canals (micro-channels in the bone), periosteum (the protective tissue lining around bone), muscle and other structures in the surgical site. Bleeding at the site is considered a favorable condition to enhance healing of the wound site by bringing to the site the patient's own cytokines, i.e., proteins and other molecules which are the body's mechanism to carry out the healing process. Any interference with the blood cell mechanism would be considered non-biocompatible and an adverse outcome.

The present invention, a bone putty with a useful bulk viscosity has been achieved by using a very high molecular weight class of soluble hydrogel biomaterial as a carrier for demineralized bone powder mixed with mineralized and/or demineralized larger bone chips and/or machined bone rods which can be mineralized or partially or fully demineralized. The use of high molecular weight hydrogels of 700,000 Daltons, preferably over one million Daltons allows the achievement of a very malleable high strength bone putty with only a 2–5% concentration of the hydrogel in the carrier. The balance of the carrier formulation is a sterile saline and sodium phosphate buffer which avoids the toxic problems with the high concentrations of the low molecular weight organic solvents of the prior art.

In order for the bone matrix to be osteoinductive, interference either from the traumatized cells or the formulation must be at a minimum, i.e., a biocompatible condition should be established and maintained. Several specific properties have been established in the formulation to create a functional and therapeutic material. These properties pertain to both physical characteristics and to the achieving of a biocompatible or physiologically friendly condition.

It can be seen that the prior art has attempted to replicate to some degree the bone putty obtained by the mixing of blood with bone particles without the problems of mixing the two together at the surgical site in non-controlled proportions and under time and space prohibitions.

The selection of high molecular weight hydrogels for the carrier allows the use of small particle size granules of demineralized allograft bone mixed together with larger chips of demineralized and/or mineralized bone and/or rods of mineralized and/or partially or fully demineralized bone. These composite materials pack better in the wound defect providing greater strength to the packed putty and induces new bone thereby allowing the bone defect to be remodeled into the natural bone of the patient.

It is an object of the invention to utilize demineralized powdered bone in a particle size that is useful to achieve the malleability characteristics that maximizes the amount of bone in the formulation in combination with larger mineralized or demineralized chips and/or mineralized or demineralized rod members to provide overall strength and initial durability to the composition.

It is an additional object of the invention to use a non toxic carrier for the bone particles and bone chips and/or bone rods which will not adversely impact on the patient.

It is also an object of the invention to create a bone defect material which can be easily handled by the physician and does not degenerate when contacting blood flow or irrigation at the surgical site.

It is another object of the invention to utilize demineralized powdered bone in a particle size which together with larger mineralized or demineralized chips and/or rod members that is useful to achieve the malleability characteristics that maximizes the amount of bone in the formulation without creating a gritty, less malleable characteristic.

It is an additional object of the invention to use a non toxic aqueous solution carrier with a sodium phosphate buffer for the respective bone elements to present the composition in a state of physiological osmolality (isotonic) at the wound site and provides a smooth bone surface.

It is also an object of the invention to create a bone defect material which can be easily handled by the physician and does not degenerate when contacting blood flow at the surgical site.

It is another object of the invention to create a bone defect material which does not interfere with healing at the wound site.

It is still another object of the invention to create a bone defect material which has a stable viscosity from 220 to 37° C.

It is an additional object of the invention to create a bone defect material with a physiological pH of 7.4.

It is yet another object of the invention to use a sodium salt with the buffered, isotonic demineralized bone composition to aid in healing at the bone defect site.

These and other objects, advantages, and novel features of the present invention will become apparent when considered with the teachings contained in the detailed disclosure which along with the accompanying drawings constitute a part of this specification and illustrate embodiments of the invention which together with the description serve to explain the principles of the invention.

DETAILED DESCRIPTION OF THE INVENTION

Figure 1:
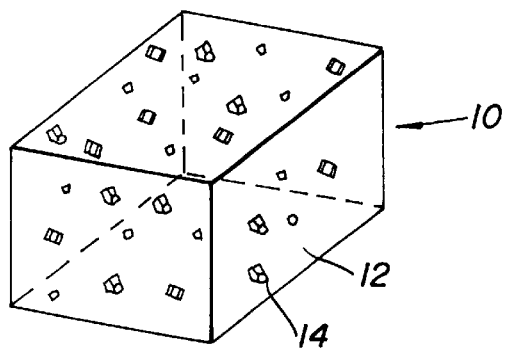
FIG. 1 is a perspective view of the invention cut into a cube with demineralized bone powder mixed with mineralized large bone chips.
Figure 2:
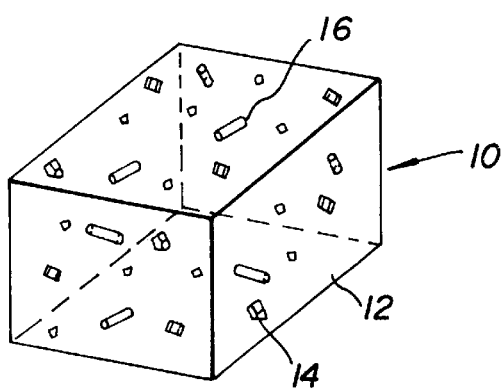
FIG. 2 is a perspective view of the invention cut into a cube with demineralized bone powder mixed with mineralized large bone chips and demineralized and/or mineralized bone rods.
Figure 3:
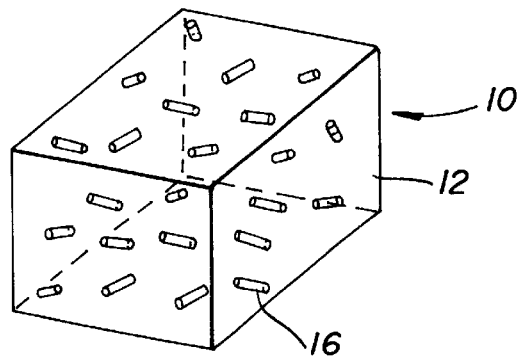
FIG. 3 is a perspective view of the invention cut into a cube with demineralized bone powder mixed with random orientated bone rods.
Figure 4:
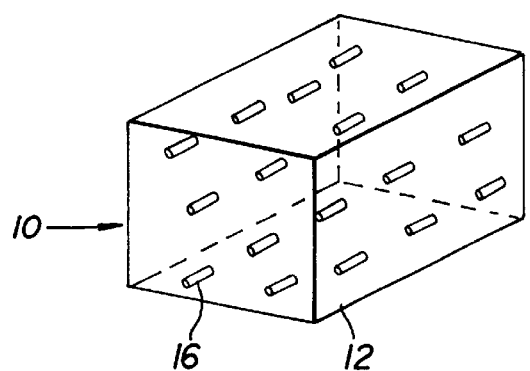
FIG. 4 is a perspective view of the invention cut into a cube with demineralized bone powder mixed with aligned bone rods.

The present invention is directed towards a composite bone composition 10 comprising a demineralized bone powder 12 mixed together with larger mineralized and/or demineralized chips 14 and/or machined bone rods 16 all of which are mineralized, partially demineralized or demineralized in a high viscosity hydrogel carrier to form a composition which can be placed in a bone defect area to heal bone defects. The preferred embodiment and the best mode as shown in FIG. 3 and for the composite bone composition is the demineralized bone powder 12 with bone rods 16. These and other embodiments of the invention overcome the two basic deficiencies of the glycerol carrier and bone particle flowable compositions currently being used in the prior art: first, the low molecular weight of the glycerol carrier; and second, the use of large cubical chunks to achieve the preferred bulk viscosity and putty strength. The types of demineralized bone powder used in the invention are cortical and corticocancellous bone powder and the larger chips are cortical and corticocancellous bone while the rods are preferably cortical bone.

Figure 5:
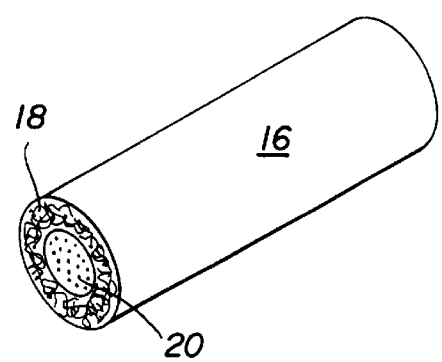
FIG. 5 is an enlarged perspective view of a rod of the invention which is partially demineralized.
Figure 6:
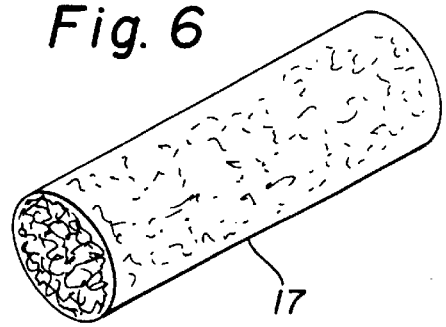
FIG. 6 is an enlarged perspective view of a rod of the invention which is fully demineralized.

It was found that adding reinforcing rods 16 of machined cortical bone in either a random or oriented manner in the putty significantly stiffens or strengthens the resultant viscous formulation. The rods 16 are made of cortical bone and are machined to a diameter of 0.4–3.0 mm, perferably 2.0 mm when left fully mineralized or a diameter ranging from 1.5 mm to about 8.0 mm when partially demineralized or demineralized. The rods have and a length of 1–10 mm with athickness to length ratio preferably of 1:3 butrangingfroml 1:2 to 1:6. The rods may be left fully mineralized or demineralized either fully or partially through surface demineralization. Fully demineralized rods 17 shown in FIG. 6 will retain their length and diameter ratio but are very flexible. Partially demineralized rods 16 as shown in FIG. 5 will retain various degrees of stiffness inversely proportional to the degree of demineralization and retention of core mass. The partially demineralized rods have a demineralized outer section 18 of exposed collagen matrix and a cortical bone core 20.

Example of Demineralized Cortical Rods
Formulation in MTF DBX Putty (DBM)

A-I: Preparation of Demineralized Cortical Rods in 4% HA Putty Carrier (30% Formulation)

A 14.0 g sample of 4% HA w/w 700,000 Daltons in phosphate buffer saline at a pH of 7.2 and 125,000 viscosity putty carrier was weighed and transferred into a 30 ml glass bottle with a lid. A 6.0 g sample of demineralized cortical pellets was weighed and transferred into the glass bottle. The formulation was mixed until it appeared uniform. After mixing, the sample equilibrated in the refrigerator for approximately one hour after which time the sample was re-mixed for an additional five minutes and was stored in the refrigerator until needed. Comments: No flow-ability in formulation.*

A-2: Preparation of 30% Demineralized Cortical Rods Formulation in 30% DBX Putty (1:1 ratio by wt.)

A 2.00 g sample of 30% demineralized cortical rod formulation was weighed and transferred into a glass bottle with a lid. A 2.00 g sample of 30% DBX Putty (30% bone w/w with 4% HA w/w 700,000 Daltons in phosphate buffer solution at a pH of 7.2 and 125,000 viscosity) was then weighed and transferred into the glass bottle. The 1:1 ratio formulation was mixed with a spatula until it appeared uniform. After mixing the formulation was placed into the refrigerator and was allowed to equilibrate for one hour. After the sample equilibrated the sample was removed from the refrigerator and was re-mixed for an additional five minutes. After additional mixing the sample was stored in the refrigerator until needed. Comments: Was better than A-1.*

A-3: Preparation of 30% Demineralized Cortical Rods Formulation in 30% DBX Putty (2:1 ratio by wt.)

Weighed a 2.00 g sample of 30% demineralized cortical rod formulation in a weighing pan and transferred it into a 30 ml glass bottle. A 1.0 g sample of 30% DBX Putty (30% bone w/w with 4% HA w/w 700,000 Daltons in phosphate buffer solution at a pH of 7.2 and 125,000 viscosity) was then weighed and transferred into the 30 ml glass bottle with the demin enlarged rods. The 2:1 formulation was mixed with a spatula until it appeared uniform. After mixing the sample was placed into the refrigerator and equilibrated for one hour. After one hour the sample was removed from the refrigerator and re-mixed for an additional five minutes. Sample was then stored in the refrigerator until needed. Comments: The consistency of the formulation was good.*

*See Table 3 for a complete list of the comments and observations.

TABLE 1

Mixing Ratio of Demineralized Cortical Rods to DBX Putty Formulation

| Sample | Material | Mixing Ratio | Calculated Weight | Actual Weight |
| --- | --- | --- | --- | --- |
| A-1 | Demin cortical rods | 30% | 6.00 g | 6.003 g |
|  | 4% HA putty carrier | 70% | 14.00 g | 14.008 g |

TABLE 1-continued

Mixing Ratio of Demineralized Cortical Rods to DBX Putty Formulation

| Sample | Material | Mixing Ratio | Calculated Weight | Actual Weight |
|---|---|---|---|---|
| A-2 | 30% Demin cortical rods in 4% HA putty carrier (A-1) | 1:1 | 2.00 g | 2.001 g |
|  | DBX Putty 30% |  | 2.00 g | 2.003 g |
| A-3 | 30% Demin cortical rods in 4% HA putty carrier (A-1) | 2:1 | 2.00 g | 2.008 g |
|  | DBX Putty 30% |  | 1.00 g | 1.005 g |

Note:
Mixing ratio for samples A-2 and A-3 is by weight.

B-I: Preparation of Demineralized Cortical/Cancellous Chips in 4% HA Putty Carrier 30% Formulation.

A 14.0 g sample of 4% HA w/w 700,000 Daltons in phosphate buffer saline at a pH of 7.2 and 125,000 viscosity putty carrier was weighed and transferred into a 30 ml glass bottle with a lid. A 6.0 g sample of demineralized cortical/cancellous chips was weighed and transferred into the glass bottle with the HA carrier. The formulation was mixed until uniformity was achieved. After initial mixing the formulation was placed into the refrigerator and was allowed to equilibrate for approximately one hour. After equilibration the formulation was removed for the refrigerator and was re-mixed for an additional five minutes. After mixing the mixture was placed back into the refrigerator until needed. Comments: Same as sample A-1.

B-2: Preparation of 30% Demineralized Cortical/Cancellous Chips Formulation in 30% DBX Putty (1:1)

A 2.00 g sample of 30% demineralized cortical/cancellous chip formulation was weighed and transferred into a 30 ml glass bottle. A 2.00 g sample of 30% DBX Putty (30% bone w/w with 4% HA w/w 700,000 Daltons in phosphate buffer solution at a pH of 7.2 and 125,000 viscosity) was weighed and transferred into the 30 ml glass bottle with the demin chips. Using a spatula the formulation was mixed until it appeared uniform. After initial mixing the sample was placed into the refrigerator and equilibrated for approx. one hour. After equilibration the sample was removed from the refrigerator and was re-mixed for an additional five minutes. The sample was then stored in the refrigerator until needed. Comments: A little better than sample B-1.*

B-3: Preparation of 30% Demineralized Cortical/Cancellous Chips Formulation in 30% DBX Putty (2:1)

A 2.00 g sample of 30% demineralized cortical/cancellous chips formulation was weighed and transferred into a 30 ml-glass bottle with lid. A 1.0 g sample of 30% DBX Putty (30% bone w/w with 4% HA w/w 700,000 Daltons in phosphate buffer solution at a pH of 7.2 and 125,000 viscosity) was weighed and mixed with the 2.00 g sample of cort/canc. chip formulation. The mixture was mixed with a spatula until it appeared uniform. After mixing the sample was placed into the refrigerator and the formulation equilibrated for approx. one hour. After the sample equilibrated, the sample was removed from the refrigerator and re-mixed for five minutes. Sample was then stored in the refrigerator until needed. Comment: Liked the consistency of the formulation.*

*See Table 3 for a complete list of the comments and observations.

TABLE 2

Mixing Ratio of Demineralized Cortical/Canc. Chips to DBX Putty Formulation

| Sample | Material | Mixing Ratio | Calculated Weight | Actual Weight |
|---|---|---|---|---|
| B-1 | Demin cort/canc. chips (4–10 mm) | 30% | 6.00 g | 6.001 g |
|  | 4% HA putty carrier | 70% | 14.00 g | 14.001 g |
| B-2 | 30% Demin cort/canc. chips in 4% HA putty carrier (B-1) | 1:1 | 2.00 g | 2.010 g |
|  | DBX putty 30% |  | 2.00 g | 2:001 g |
| B-3 | 30% Demin cort/canc. chips in 4% HA putty carrier (B-1) | 2:1 | 2.00 g | 2.005g |
|  | DBX Putty 30% |  | 1.00 g | 1.000 g |

Alternatively, the combination of the 250–750 micron particle size of demineralized, lyophilized, allograft bone when mixed with mineralized bone chips ranging from 0.1 to 10.0 mm in size and/or bone rods with a length of 1.0 to 10 mm in very low concentrations of high molecular weight hydrogels in a suitable carrier produces a malleable putty with clinically useful bone inducing properties. The malleable property permits the surgeon to shape the quantity of bone putty to exactly fit the surgical defect while providing a higher strength and durability to the bone putty.

It was also discovered that high molecular weight viscous carriers can be used to contain the demineralized bone matrix in the simple, smaller ground particle formed together with mineralized or demineralized cortical-cancellous chips or particles of a relative larger size (0.1–10 mm) provides a wash resistant means of introducing the putty to the surgical site. The large, mineralized chips give the composition mixture body and substance to provide some resistance to load and displacement. The chip/ground particle combination preferably accounts for 20–45% by weight of the putty composition.

The rods, chips and demineralized bone powder are mixed into a hydrogel viscous carrier such as Hyaluronic acid, chitosan, collagen (allogeneic or xenogeneic) or other high molecular weight viscous carriers. The ideal carriers for the malleable putty are preferably taken from high molecular weight hydrogels such as 1) Sodium Hyaluronate about $7.0 \times 10^5$–$3.0 \times 10^6$ Daltons; 2) Chitosan about $1.0 \times 10^5$–$3.0 \times 10^5$ Daltons; Chitosan in a higher molecular weight over $1.0 \times 10^6$ Daltons can also be used in the invention; and 3) CMC-carboxy-methyl-cellulose.

TABLE 3

4 mm Cortical Rods and Cortical/Cancellous chips in DBX Formulations

| Sample | Material | Observations |
|---|---|---|
| A-1 | Demineralized cortical rods (4 mm) in 4% HA carrier (30%) | Rods were too hard. No flow-ability in formulation. |
| A-2 | Demineralized cortical rods (4 mm) in 4% HA carrier mixed with 30% DBX Putty 1:1 | This sample a little better than sample A-1. |
| A-3 | Demineralized cortical rods (4 mm) in 4% HA carrier mixed with 30% DBX Putty 2:1 | Good consistency of the formulation. |
| B-1 | Demineralized Cortical/Cancellous Chips (4–10 mm) in 4% HA putty carrier (30%) | Same as sample A-1. No flow-ability in the sample, too much hard bone in mixture. |

TABLE 3-continued 4 mm Cortical Rods and Cortical/Cancellous chips in DBX Formulations

| Sample | Material | Observations |
|---|---|---|
| B-2 | Demineralized Cortical/Cancellous Chips (4–10 mm) in 4% HA putty carrier mixed with 30% DBX Putty 1:1 | A little better than sample B-1. |
| B-3 | Demineralized Cortical/Cancellous Chips (4–10 mm) in 4% HA putty carrier mixed with 30% DBX Putty 2:1 | Good consistency of the formulation |

The rod/ground particle combination perferably accounts for 10–35% by weight of the putty composition. The rods may be mixed into the viscous carrier in a random fashion and one aspect of this invention is to retain the random nature and orientation of the rods in the carrier. Another aspect of the invention is to orient the rods. This is accomplished by extruding the viscous mass containing the rods through a coarse filter comprised of a row of rigid teeth openings analogous to a rake. The spacing between the blades of the rake may vary to be just greater than the rod diameter or to larger spacing which will cause variations in the degree of orientation. The resultant viscous mixture containing the fully or partially oriented rods would then be placed in a suitable container, such as a syringe with a wide bore mouth or an open jar type container. The surgeon would then remove the viscous material containing the rods, place them in the bony defect where they will remain in place during the healing process. The presence of the oriented rods will provide a degree of resistance to bearing loads greater than would be present without the oriented or random positioned rods.

The natural condition for blood plasma as well as synovial fluid, cerebrospinal fluid, aqueous humor (fluid within the globe of the eye) is at a pH of 7.3–7.4 (reference, *Principles of Biochemistry*, Chapters 34 & 35, White, Handler and Smith, McGraw Hill, NY, 1964). At very slight changes in pH, blood cells will shift their equilibrium of hemoglobin. This hemoglobin concentration will change over the small pH range of 7.3 to 7.7 (White et al p. 664). In addition, at significantly lower pH values in the acidic range, protein molecules will denature, i.e., degrade. Thus, it is important to maintain any surgical implant which is intimate contact with blood at a biocompatible condition of about pH 7.2–7.4.

It is important to note that the body has many complex and redundant mechanisms to maintain its biochemical balance. The blood pH can be adjusted by several means to its normal, physiologic pH. Hence the presence of a nonphysiologic material at the site of a bleeding bone wound will eventually be overcome and any non-biocompatible condition will return to normal pH. However, the present invention formulation can start out and maintain physiologic pH without stressing the body's biochemical mechanisms when the bone composition material is applied at the wound site.

In achieving physiologic pH, the formulation uses a phosphate buffer based on an aqueous system of the two phosphate anions, $HPO_4^{-2}$ and $H_2PO_4^{-1}$ when the hydrogel used is sodium hyaluronate. Sodium hyaluronate in the form of the sodium salt is generally described as an acid mucopolysaccharide. This buffer system is used both to neutralize any residual acid used to demineralize the bone and to buffer the sodium hyaluronate viscous hydrogel carrier. It is important to neutralize the acid (hydrochloric acid) used to demineralize the bone so as to assure that there is no residue of this very strong acid which could overwhelm the buffering capacity of the phosphate system used to buffer the sodium hyaluronate carrier.

The pH is adjusted to the physiologic 7.2–7.4 pH by using either or both of dibasic sodium phosphate or monobasic sodium phosphate and adjusting the solution with saline, i.e., a sodium chloride solution. The sodium chloride is chosen instead of only water so as to control the final osmolality of the formulation to preclude dehydration of the surrounding cells.

When the hydrogel is sodium hyaluronate the composition uses sodium salts of the phosphate buffer. This is to create an equilibrium system at the wound site which will draw in calcium ions necessary to grow new bone. The mechanism to achieve this is based on the LeChatelier corollary to the Principle of Chemical Equilibrium: When a factor (temperature, pressure, concentration, etc.) determining the equilibrium of a system is altered, the system tends to change in such a way as to oppose and partially annul the alteration in this factor. (reference, *General Chemistry*, McCutcheon, Seltz and Warner, Van Nostrand, N.Y., 1944; p. 248).

This principal manifests at the bone wound site as follows: The buffer introduced contains sodium and phosphate ions which will remain in solution due to the high solubility of sodium phosphate. Calcium ions in the extracellular fluid will react with the phosphate ions to result in the precipitation of insoluble calcium phosphate salt. More phosphate ions will ionize from the associated state of the phosphate buffer to introduce more phosphate ions that will, in turn react with more calcium and precipitate yet more insoluble calcium phosphate. The calcium phosphate will deposit at the wound site where the buffered formulation was placed by the surgeon. This results in an increase in the presence of calcium at the wound site. The bone regeneration mechanism will utilize calcium starting 7–10 days after the wound starts healing by the well-known osteochondral healing mechanism. Hence, the selection of the sodium phosphate buffer to achieve the physiologic pH provides a means to increase the calcium concentration in the precise location where calcium will be needed to grow new bone.

Thus, the presence of soluble calcium is induced at the bone defect site. This will encourage new bone growth through the normal biochemical mechanism. Soluble calcium can be attracted to the surgical site by using a sodium phosphate buffer of pH 6.8–7.2 in lieu of isotonic saline. The phosphate buffer attracts calcium cations to the site from the surrounding healthy bone and creates an equilibrium concentration of the calcium precisely at the site of healing where it is most desirable to grow new bone.

It is a well known principal of physiology that osmotic pressure must be maintained within a narrow range to assure healthy conditions for the many cell types present in normal or surgically wounded cells. The condition of normal osmotic pressure is referred to as an isotonic state and is quantified in humans by the value of about 300 mOsmol/Kg. The sodium hyaluronate (HA) formulation and other applicable hydrogels are buffered to isotonic conditions using sodium chloride as the ionic salt to supplement the sodium phosphate. Were the sodium hyaluronate formulation to be buffered without the supplemental saline, the final hydrogel would only reach an osmolality of less than 50 mOsmol/Kg.

At this low osmolality, the extra cellular environment at the wound site would be in a state of hypotonicity and result in the inflow of large quantities of water to the cells and blood cells at the wound site to normalize the osmotic pressure. This will result in a greater than optimum degree of hydration of the cells and inhibit wound healing in general and bone growth in particular. Hemolysis may occur due to excess fluid in the cells.

Other, commercial bone defect fillers are either non-isotonic or worse, are completely anhydrous. The anhydrous state will result in a massive hydration of the site. This will result in an edematous condition. This condition would result in both diluting the demineralized bone matrix (washes it away) and massive dilution of the extracellular fluids. On a macro level, edema is seen as swelling at the site and may be painful to the patient.

The subject formulation has been tested for resistance to hemolysis in a test based on direct blood contact; the results were negative, i.e., the formulation was found to be non-hemolytic. The commercial, anhydrous formulation based on anhydrous glycerol is hemolytic by the same test protocol. The observation of hemolytic behavior by the glycerol based commercial bone filler may be due to the acidic pH (about 4.5) alone, or to a combination of the acidic pH and the non-isotonic state of the material as it enters the wound site.

It is envisioned that suitable amounts of bone morphogenic proteins (BMP) can be added to the putty via demineralized bone powder, rods, etc. at any stage in the mixing process to induce accelerated healing at the bone site. BMP directs the differentiation of pluripotential mesenchymal cells into osteoprogenitor cells which form osteoblasts. The ability of freeze dried demineralized cortical bone to facilitate this bone induction principle using BMP present in the bone is well known in the art. However, the amount of BMP varies in the bone depending on the age of the bone donor and the bone processing. Sterilization is an additional problem in processing human bone for medical use as boiling, autoclaving or irradiation over 2.0 mrads is sufficient to destroy or alter the BMP present in the bone matrix.

Another embodiment of the invention is to induce the presence of soluble calcium at the bone defect site. This will encourage new bone growth through the normal biochemical mechanism. Soluble calcium can be attracted to the surgical site by using a sodium phosphate buffer of pH 7.2 in lieu of the isotonic saline. The phosphate buffer will attract calcium cations to the site from the surrounding healthy bone and create an equilibrium concentration of the calcium precisely at the site of healing where it is most desirable to grow new bone.

Any number of medically useful substances can be incorporated in the invention by adding the substances to the composition at any steps in the mixing process or directly to the final composition. Such substances include collagen and insoluble collagen derivatives, hydroxy apatite and soluble solids and/or liquids dissolved therein. Also included are antiviricides such as those effective against HIV and hepatitis; antimicrobial and/or antibiotics such as erythromycin, bacitracin, neomycin, penicillin, polymyxin B, tetracycline, viomycin, chloromycetin and streptomycin, cefazolin, ampicillin, azactam, tobramycin, clindamycin and gentamycin. It is also envisioned that amino acids, peptides, vitamins, co-factors for protein synthesis; endocrine tissue or tissue fragments; synthesizers; enzymes such as collagenase, peptidases, oxidases; polymer cell scaffolds with parenchymal cells; angiogenic drugs and polymeric carriers containing such drugs; collagen lattices; biocompatible surface active agents, antigenic agents; cytoskeletal agents; cartilage fragments, living cells such as chondrocytes, bone marrow cells, mesenchymal stem cells, natural extracts, tissue transplants, bioadhesives, transforming growth factor (TGF-beta), insulin-like growth factor (IGF-1); growth hormones such as somatotropin; bone digestors; antitumor agents; fibronectin; cellular attractants and attachment agents; immuno-suppressants; permeation enhancers, e.g. fatty acid esters such as laureate, myristate and stearate monoesters of polyethylene glycol, enamine derivatives, alpha-keto aldehydes can be added to the composition.

The invention can best be understood by the following examples with the percentages being determined by weight. All examples could also be done in an aseptic environment to maintain a sterile final product.

EXAMPLES OF THE INVENTION

Example I

A malleable putty of 4% solution Sodium Hyaluranate w/w 1,000,000+Daltons in phosphate buffered saline at a pH of about 7.2 and 140,000 viscosity with 250–750 micron demineralized cortical allograft bone powder ranging from 15% to 30% (preferably 20%) by weight of the composition has added to it mineralized bone chips ranging from 0.1 mm–10 mm in size and ranging from 5% to 20% (preferably 15%) by weight of the composition.

Example II

A malleable putty of 4% solution Sodium Hyaluranate w/w 1,000,000 Daltons in phosphate buffered saline at a pH of about 7.2 and a 140,000 viscosity with 250–750 micron demineralized cortical allograft bone powder ranging from 15% to 30% (preferably 25%) by weight of the composition has added to it mineralized bone rods ranging from 0.1 mm–10 mm in length and ranging from 5% to 20% (preferably 10%) by weight of the composition.

Example III

A malleable putty of 4% solution Hyaluronic Acid w/w 1,000,000 Daltons in phosphate buffered saline at a pH of about 7.2 and a 140,000 viscosity with 250–750 micron cortical allograft bone powder ranging from 15% to 30% by weight of the composition has added to it mineralized bone chips ranging from 0.1 mm–10 mm in size and mineralized rods ranging from 0.1 mm to 10 mm in size ranging from 5% to 25% by weight of the composition.

Example IV

A malleable putty of 5% solution chitosan with 250–750 micron demineralized cortical allograft bone powder ranging from 15% to 30% by weight of the composition has added to it mineralized bone chips ranging from 0.1 mm–10 mm in size and ranging from 5% to 20% by weight of the composition.

Example V

A malleable putty of 2–5% solution Sodium Hyaluranate w/w 1,000,000 Daltons in phosphate buffered saline at a pH of about 7.2 and 140,000 viscosity with 250–750 micron cortical allograft bone powder ranging from 15% to 30% by weight of the composition has added to it fully and partially demineralized rods ranging from 0.1 mm–10 mm in length and ranging from 5% to 20% by weight of the composition.

While the above noted examples show specific percentages of the high molecular matrix hydrogel, acceptable ranges of the same can range from 2% to 5%.

The mixing of the demineralized bone powder and mineralized or demineralized bone chips and/or rods into hydrogel solution is undertaken in a sterile chamber. The mixed malleable bone composition is then placed in a sterile container such as an impervious syringe barrel or vial, sealed and placed in a sterile sealed package.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What we claim is:

1. A sterile malleable bone composition for application to a bone defect site to promote new bone growth at the site comprising a mixture of demineralized osteogenic or osteoconductive bone powder with a particle size ranging from about 250 to about 750 microns and osteogenic bone chips of a larger size ranging from 0.1 to 10 mm in a carrier, the demineralized bone powder ranging from about 15% to about 35% of the weight of the composition and the osteogenic bone chips ranging from 5% to about 20% of the weight of the composition, the carrier being selected from a aqueous sodium based phosphate buffered solution and a hydrogel consisting of a mucopolysaccharide, said mucopolysaccharide having a high molecular weight ranging from seven hundred thousand to three million Daltons and ranging from about 2.0% to about 5.0% by weight of the carrier solution, said composition having a pH ranging from about 7.2 to about 7.4.

2. A sterile malleable bone composition as claimed in claim 1 wherein said composition includes added bone morphogenic proteins.

3. A sterile malleable bone composition as claimed in claim 1 wherein said phosphate includes two phosphate ions $HPO_4^{-2}$ and $H_2PO_4^{-1}$.

4. A sterile malleable bone composition as claimed in claim 1 wherein said composition has an isotonic state of about 300 mOsmol/Kg.

5. A sterile malleable bone composition as claimed in claim 1 comprising the addition of a calcium salt to the carrier.

6. A sterile malleable bone composition as claimed in claim 1 wherein the balance of the carrier formulation contains a sodium phosphate buffer and has a pH of about 7.2.

7. A sterile malleable bone composition as claimed in claim 1 wherein said bone powder is cortical allograft bone powder.

8. A sterile malleable bone composition as claimed in claim 1 wherein said bone powder is cortical-cancellous allograft bone powder.

9. A sterile malleable bone composition as claimed in claim 1 wherein said bone chips are cortical allograft bone chips.

10. A sterile malleable bone composition as claimed in claim 1 wherein said bone chips are cortical-cancellous allograft bone chips.

11. A sterile malleable bone composition as claimed in claim 1 wherein said bone chips are mineralized allograft bone chips.

12. A sterile malleable bone composition as claimed in claim 1 wherein said bone chips are demineralized allograft bone chips.

13. A sterile malleable bone composition as claimed in claim 1 wherein antimicrobial and/or antibiotics selected from the group consisting essentially of erythromycin, bacitracin, neomycin, penicillin, polymyxin B, tetracycline, viomycin, chloromycetin and streptomycin, cefazolin, ampicillin, azactam, tobramycin, clindamycin and gentamycin are added to said composition.

14. A sterile malleable bone composition as claimed in claim 1 wherein said hydrogel is sodium hyaluronate.

15. A sterile malleable bone composition as claimed in claim 1 wherein said hydrogel is chitosan.

16. A sterile malleable bone composition as claimed in claim 1 wherein said composition has a pH ranging from 6.8 to 7.4.

17. A sterile malleable bone composition as claimed in claim 1 wherein the aqueous solution includes an ionic salt based phosphate buffer.

18. A sterile malleable bone composition as claimed in claim 1 wherein said hydrogel has a molecular weight of at least 700,000 Daltons.

19. A sterile malleable bone composition as claimed in claim 1 wherein said hydrogel has a molecular weight of at least of 1,000,000 Daltons.

20. A sterile malleable bone composition as claimed in claim 1 wherein said hydrogel consists of the group of sodium hyaluronate and chitosan.

21. A sterile malleable bone composition as claimed in claim 1 wherein said hydrogel substantially maintains its viscosity from 22–37 degrees C.

22. A sterile malleable bone composition as claimed in claim 1 wherein said aqueous solution is saline.

23. A sterile malleable bone composition for application to a bone defect site to promote new bone growth at the site comprising a carrier and a mixture of demineralized osteogenic bone powder with a particle size ranging from about 250 to about 1000 microns and cortical bone rods having a length ranging from 1 mm to about 10 mm and a thickness to length ratio ranging of about 1:2 to 1:20, the demineralized bone powder ranging from about 15 to about 30% of the weight of the composition and the cortical bone rods ranging from 5% to about 20% of the weight of the composition, said carrier comprising a hydrogel selected from a group consisting of sodium hyaluronate, chitosan and carboxy-methyl-cellulose in saline phosphate buffer solution, said hydrogel having a high molecular weight ranging from about seven hundred thousand to about three million Daltons and ranging from about 2.0% to about 5.0% by weight of the carrier solution, said composition having a substantially neutral osmolality.

24. A sterile malleable bone composition as claimed in claim 23 wherein said composition mixture includes added bone morphogenic proteins.

25. A sterile malleable bone composition as claimed in claim 23 wherein said phosphate buffer includes two phosphate ions $HPO_4^{-2}$ and $H_2PO_4^{-1}$.

26. A sterile malleable bone composition as claimed in claim 23 wherein said composition has an isotonic state of about 300 mOsmol/Kg.

27. A sterile malleable bone composition as claimed in claim 23 wherein said bone rods are orientated in one direction in said composition.

28. A sterile malleable bone composition as claimed in claim 23 wherein antimicrobial and/or antibiotics selected from the group consisting essentially of erythromycin, bacitracin, neomycin, penicillin, polymyxin B, tetracycline, viomycin, chloromycetin and streptomycin, cefazolin, ampicillin, azactam, tobramycin, clindamycin and gentamycin are added to said composition.

29. A sterile malleable bone composition as claimed in claim 23 wherein said hydrogel has a molecular weight of at least one million Daltons.

30. A sterile malleable bone composition as claimed in claim 23 wherein said bone rods have a diameter ranging from 0.4 mm to about 2.0 mm.

31. A sterile malleable bone composition as claimed in claim 23 wherein said cortical bone rods are partially demineralized.

32. A sterile malleable bone composition as claimed in claim 31 wherein said bone rods have a diameter ranging from 3.0 mm to about 5.00 mm.

33. A sterile malleable bone composition as claimed in claim 23 wherein said cortical bone rods are fully demineralized and flexible.

34. A sterile malleable bone composition as claimed in claim 23 wherein said cortical bone rods are randomly orientated in said composition.

35. A sterile malleable bone composition for application to a bone defect site to promote new bone growth at the site comprising a carrier and a mixture of demineralized osteogenic bone powder with a particle size ranging from about 250 to about 750 microns and surface demineralized cortical bone rods having a diameter ranging from 1.0 mm to 5.00 mm with a diameter to length ratio ranging from 1:2 to 1:20, the demineralized bone powder ranging from about 25 to about 30% of the weight of the composition and the cortical bone rods ranging from 5% to about 10% of the weight of the composition, said carrier comprising a high molecular weight hydrogel mucosaccharide in aqueous phosphate buffered solution, said mucosaccharide having a high molecular weight over 700,000 Daltons and ranging from about 2.0% to about 5.0% by weight of the carrier solution.

36. A sterile malleable bone composition as claimed in claim 35 wherein said cortical bone rods are randomly oriented in said composition.

37. A sterile malleable bone composition as claimed in claim 35 wherein said cortical bone rods are oriented in one direction in said composition.

38. A sterile malleable bone composition for application to a bone defect site to promote new bone growth at the site comprising a carrier and a mixture of demineralized osteogenic bone powder with a particle size ranging from about 250 to about 1000 microns and mineral cortical bone rods having a diameter ranging from 0.4 to about 2.0 mm and a diameter to length ratio of about 2- to about 6, the demineralized bone powder ranging from about 25 to about 35% of the weight of the composition and the mineralized cortical rods ranging from 5% to about 25% of the weight of the composition, said carrier comprising a hydrogel selected from a group consisting of sodium hyaluronate, chitosan and carboxy-methyl-cellulose in a buffered phosphate saline solution, said hydrogel having a high molecular weight of at least $1.0$–$10^6$ Daltons and ranging from about 1.0% to about 5.0% by weight of the carrier solution.

39. A sterile malleable bone putty composition for application to a bone defect site to promote new bone growth at the site which comprises a new bone growth inducing mixture of demineralized lyophilized allograft bone powder with a particle size ranging from about 250 to about 750 microns and mineralized cortical allograft bone chips ranging from 1.0 mm to 10.00 mm in size and cortical bone rods in a hyaluronic acid saline phosphate buffer carrier, the hyaluronic acid component ranging from above 2.0% to about 5% of the carrier solution and having a molecular weight of at least $1.0 \times 10^6$ Daltons, the total bone content of the bone powder, bone chips and bone rods in the carrier ranging in weight from about 30% to about 50% total weight of the composition.

40. A sterile malleable bone putty composition for application to a bone defect site to promote new bone growth at the site comprising a new bone growth inducing demineralized lyophilized allograft bone powder with a particle size ranging from about 250 to about 750 microns and mineralized bone chips ranging from 0.1 mm–10 mm in a high molecular weight sodium hyaluronate and saline carrier with a phosphate buffer, the bone content of the composition ranging from about 25% to about 45% by weight and the high molecular weight sodium hyaluronate component ranges from about 2% to about 5% of the carrier and has a molecular weight greater than one million Daltons.

41. A sterile malleable bone putty composition for application to a bone defect site to promote new bone growth at the site which comprises a new bone growth inducing demineralized lyophilized allograft bone powder with a particle size ranging from about 250 to about 750 microns and mineralized bone chips ranging from 1–10 mm in size in a carrier solution, said carrier solution comprising a high molecular weight chitosan having a molecular weight over $1.0 \times 10^5$ Daltons in an aqueous buffered phosphate with the bone content of the putty composition ranging from about 30% to about 35% and the chitosan component ranging from 2 to 5% of the carrier solution and said composition having a substantially neutral osmolality.

42. A sterile malleable bone putty composition for application to a bone defect site to promote new bone growth at the site which comprises a new bone growth inducing demineralized lyophilized allograft bone powder with a particle size ranging from about 250 to about 750 microns and mineralized bone cordical bone rods having a diameter to length ratio ranging from 1:2–1:20 mm in length in a carrier, said carrier comprising a high molecular weight chitosan having a molecular weight over $1.0 \times 10^6$ Daltons in a water phosphate buffered solution with the bone content of the putty composition ranging from about 30% to about 35% and the chitosan component ranging from 2 to 5% of the carrier solution and said composition having a substantially neutral osmolality.

43. A sterile malleable bone putty as claimed in claim 42 wherein said cortical bone rods are mineralized.

44. A sterile malleable bone putty as claimed in claim 42 wherein said cortical bone rods are partially demineralized.

45. A sterile malleable bone putty as claimed in claim 42 wherein said cortical bone rods are fully demineralized.

46. A sterile malleable bone putty composition for application to a bone defect site to promote new bone growth at the site which comprises a new bone growth inducing demineralized lyophilized allograft bone powder with a particle size ranging from about 250 to about 750 microns and mineralized bone cordical bone rods having a diameter to length ratio ranging from 1:2–1:20 mm in length in a high molecular weight carboxy-methyl-cellulose phosphate buffered water carrier solution with the bone content of the putty composition ranging up to 30% and the carboxy-methyl-cellulose component ranging from 2 to 5% by weight of the carrier solution.

47. A sterile malleable bone putty as claimed in claim 46 wherein said cortical bone rods are mineralized.

48. A sterile malleable bone putty as claimed in claim 46 wherein said cortical bone rods are partially demineralized.

49. A sterile malleable bone putty as claimed in claim 46 wherein said cortical bone rods are fully demineralized.

* * * * *